(12) United States Patent
Iwasaki et al.

(10) Patent No.: US 11,787,973 B2
(45) Date of Patent: Oct. 17, 2023

(54) SLIDING MEMBER AND METHOD FOR MANUFACTURING SAME

(71) Applicant: ASAHI FR R&D CO., LTD., Saitama (JP)

(72) Inventors: Kosho Iwasaki, Saitama (JP); Kazuaki Yamaguchi, Saitama (JP)

(73) Assignee: ASAHI FR R&D CO., LTD., Saitama (JP)

( * ) Notice: Subject to any disclaimer, the term of this patent is extended or adjusted under 35 U.S.C. 154(b) by 0 days.

(21) Appl. No.: 17/765,403

(22) PCT Filed: Sep. 25, 2020

(86) PCT No.: PCT/JP2020/036377
§ 371 (c)(1),
(2) Date: Mar. 30, 2022

(87) PCT Pub. No.: WO2021/065737
PCT Pub. Date: Apr. 8, 2021

(65) Prior Publication Data
US 2022/0380625 A1 Dec. 1, 2022

(30) Foreign Application Priority Data
Sep. 30, 2019 (JP) .................... 2019-180635

(51) Int. Cl.
*C09D 183/06* (2006.01)
*C09D 7/63* (2018.01)

(52) U.S. Cl.
CPC ............ *C09D 183/06* (2013.01); *C09D 7/63* (2018.01)

(58) Field of Classification Search
None
See application file for complete search history.

(56) References Cited

U.S. PATENT DOCUMENTS 4,889,770 A 12/1989 Ona et al.
9,284,413 B2 * 3/2016 Larson .................. C08G 77/38
(Continued)

FOREIGN PATENT DOCUMENTS

| JP | S58-183170 A | 10/1983 |
| JP | H0195156 A | 4/1989 |
| JP | H02229837 A | 9/1990 |
| JP | 2006511637 A | 4/2006 |

(Continued)

OTHER PUBLICATIONS

Dec. 8, 2020 International Search Report issued in International Patent Application No. PCT/JP2020/36377.
(Continued)

*Primary Examiner* — Stefanie J Cohen
(74) *Attorney, Agent, or Firm* — Oliff PLC

(57) ABSTRACT

A sliding member which has low sliding resistance, can prevent the leakage of a liquid, has low dust emission properties and low leachability, and can be manufactured in a simple manner; and a method for manufacturing the sliding member. The sliding member includes an elastic molded body which is coated with a coating layer composition containing an amino-modified silicone compound having a silanol group and/or an alkoxysilyl group and also having an amino-containing group in a side chain. The method for manufacturing the sliding member includes the steps of: preparing the coating layer composition containing the amino-modified silicone compound having the silanol group and/or the alkoxysilyl group and also having the amino-containing group in a side chain; applying the coating layer composition to the elastic molded body; and coating the elastic molded body with the coating layer composition.

11 Claims, 1 Drawing Sheet

(56) References Cited

U.S. PATENT DOCUMENTS

| | | | |
|---|---|---|---|
| 10,722,450 B2 * | 7/2020 | Champeaux | A61Q 5/06 |
| 2004/0115444 A1 | 6/2004 | Janssen et al. | |
| 2006/0122413 A1 * | 6/2006 | Schafer | D06M 15/6436 |
| | | | 556/413 |
| 2006/0222870 A1 | 10/2006 | Inokuchi | |
| 2007/0073028 A1 * | 3/2007 | Hupfield | C08G 77/388 |
| | | | 525/474 |
| 2007/0299402 A1 * | 12/2007 | Ishii | A61L 27/303 |
| | | | 525/477 |
| 2010/0324501 A1 * | 12/2010 | Horiuchi | A61M 5/31513 |
| | | | 604/222 |
| 2011/0124803 A1 * | 5/2011 | Yamamoto | D06M 15/657 |
| | | | 524/588 |
| 2011/0276005 A1 | 11/2011 | Hioki et al. | |
| 2012/0178324 A1 * | 7/2012 | Behnam | D06M 15/6436 |
| | | | 524/588 |
| 2019/0317438 A1 * | 10/2019 | Sambhy | G03G 15/2025 |
| 2020/0338272 A1 | 10/2020 | Yotsutsuji | |

FOREIGN PATENT DOCUMENTS

| | | | | |
|---|---|---|---|---|
| JP | 2006312713 A | 11/2006 | | |
| WO | 2010064667 A1 | 6/2010 | | |
| WO | WO-2013020173 A1 * | 2/2013 | | A61L 15/08 |
| WO | 2017168461 A1 | 10/2017 | | |

OTHER PUBLICATIONS

Dec. 8, 2020 Written Opinion issued in International Patent Application No. PCT/JP2020/36377.
Apr. 5, 2022 International Preliminary Examination Report issued in International Patent Application No. PCT/JP2020/36377.
Nov. 18, 2021 Office Action issued in Japanese Patent Application No. 2021-551195.
Nov. 24, 2021 Notice of Reasons for Refusal issued in Japanese Patent Application No. 2021-551195.
Jan. 11, 2022 Decision to Grant issued in Japanese Patent Application No. 2021-551195.

* cited by examiner

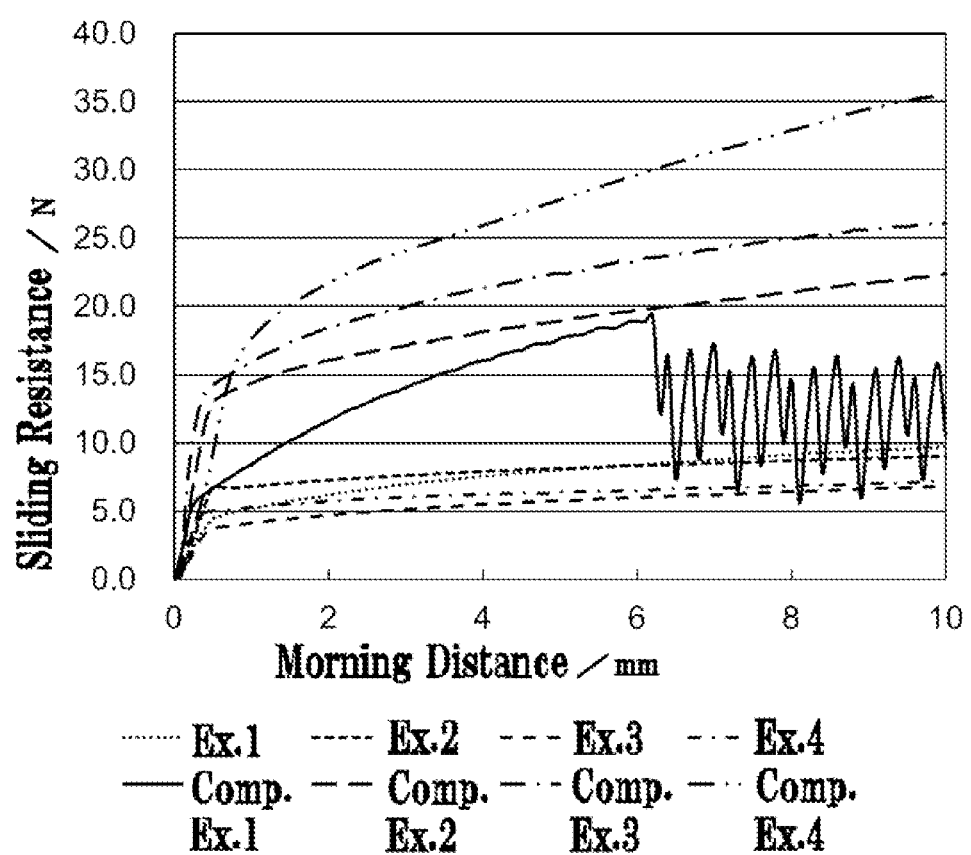

SLIDING MEMBER AND METHOD FOR MANUFACTURING SAME

TECHNICAL FIELD

The present invention relates to a sliding member which can be used for a gasket of a syringe, packing, O-ring, or the like and exhibits excellent slidable and liquid-tight properties, and a method for manufacturing same.

BACKGROUND ART

Syringes which inject a liquid medicine into patients after inhaling it and then pushing it out during medical practice, pre-filled syringes which inject a pre-sealed liquid medicine into patients or into an infusion solution by pushing it out during practice, and syringes for blood drawing when donating or testing are all equipped with an inserted gasket which is installed at the tip of a plunger inside of their syringe cylinders. These gaskets are required not to leak to or from the syringe tubes when a liquid medicine or blood is inhaled and drained, maintaining liquid sealing without creating gaps and with stable slidability.

In addition, packing and O-rings which are attached to the drain port of a liquid transfer tube or liquid container are also required not only to possess smooth slidability when attached to tubes and containers but also to maintain fluid integrity to protect from accidental fluid leaks.

As such a slidable elastic molded body including gasket, packing and O-rings, to reduce friction and to improve slidability, a silicone oil was previously applied or configured to bleed to it.

For example, Patent Document 1 discloses that a syringe comprises a barrel made of a resin, a gasket which is freely inserted into the barrel with slidability, a plunger installed in the gasket, and a silicone membrane coated with a silicone oil with a kinematic viscosity of 500-100,000 cSt relative to the inner circumference of the barrel and with a coating weight of 5-50 Hg per 1 cm² area.

In addition, Patent Document 2 discloses that a high-slidability syringe comprising:
a syringe barrel;
a gasket adapted to be press-fitted in the syringe barrel and used in a sliding manner in the syringe barrel; and
a piston rod with the gasket attached to a front end thereof, wherein the gasket comprises: a gasket main body that is formed of a rigid plastic having resistance to a drug solution to be loaded into the syringe barrel and has a recessed groove formed in a sliding contact surface thereof adapted to slidably contact an inner circumferential surface of the syringe barrel; and a sliding contact ring that is fitted in the recessed groove, the sliding contact ring comprises: a rubber base material that, when silicone oil is added thereto, allows the silicone oil to bleed therefrom under increased pressure on the sliding contact ring against the syringe barrel; and the silicone oil added to the rubber base material.

In recent years, syringes and other products have become more sophisticated, and hence sliding members which express a lower sliding resistance and better slidable properties, do not leak, nor do not cause dust from impurities such as solid particles, and can be easily manufactured are required compared with those of conventional members such as a slidable gasket.

PRIOR ART DOCUMENT

Patent Document

[Patent Document 1] WO2010/064667
[Patent Document 2] WO2017/168461

SUMMARY OF INVENTION

Problem to be Solved by the Invention

The present invention is made to solve the problems, and its object is to provide a sliding member which has low sliding resistance, can prevent the leakage of a liquid, has low dust emission properties and low leachability, and can be manufactured in a simple manner; and a method for manufacturing the sliding member.

Means to Solve the Above Problems

A sliding member described in the scope of the patent claim developed to achieve the objects described above comprises an elastic molded body which is coated with a coating layer composition containing an amino-modified silicone compound having a silanol group and/or an alkoxysilyl group and also having an amino-containing group in a side chain.

In the sliding member, the elastic molded body is preferably an elastic molded body including at least one of a rubber ingredient selected from the group consisting of butyl rubber and halogenated butyl rubber.

In the sliding member, the amino-modified silicone compound has, for example, the silanol group and/or a $SiOR^{1'}$ group (provided that $R^{1'}$ is a hydrogen group, a methyl group, an ethyl group and/or a n-propyl group) as the alkoxysilyl group.

In the sliding member, the amino-modified silicone compound has preferably the silanol group and/or the alkoxysilyl group at one or both terminals of the main chain thereof.

In the sliding member, the amino-modified silicone compound has preferably siloxane-repeating units which are presented with the following chemical formula (1):

[Chemical expression 1]

(in the chemical formula (1), $-R^2$ and $-R^3$ are independently an alkyl group having 1-3 carbons or a phenyl group); siloxane-repeating units having the amino-containing group which are presented with the following chemical formula (2):

[Chemical expression 2]

(in the chemical formula (2), $-R^4$ is an alkyl group having 1-3 carbons or a phenyl group; $-R^5$ is $-U^1-N(-R^a)-V^1-N(-R^b)-W^1-NH(-R^c)$, $-U^2-N(-R^d)-V^2-NH(-R^e)$ or $-U^3-NH(-R^f)$ (providing that $-U^1$-, $-U^2$-, $-U^3$-, $-V^1$-, $-V^2$-, and $-W^1$- are $-(CH_2)_x-$ (providing that x is a number of 2-4), or $-(CH_2)_{y1}-(CH(CH_3))_{y2}-(CH_2)_{y3}-$ (providing that y1 and y2 are a number of 0-4, y3 is a number of 1-4); $-R^a$, $-R^b$, $-R^c$, $-R^d$, $-R^e$, and $-R^f$ are independently a hydrogen atom, $-(CH_2)_z-CH_3$ (providing that z is a number of 0-3), or $-(CH_2CH(OH)CH_2(OH))$; and silanol units having the silanol group and/or alkoxysilyl group which are presented with the following chemical formula (3):

[Chemical expression 3]

(3)

(in the chemical formula (3), $-R^1$ is a hydrogen group, a methyl group, an ethyl group, or an n-propyl group; $-R^6$ is an alkyl group having 1-3 carbons or a phenyl group; $-R^7$ is an alkyl group having 1-3 carbons, a phenyl group, or a binding moiety).

In the sliding member, the amino-modified silicone compound has more preferably a compound which is presented with the following chemical formula (4):

[Chemical expression 4]

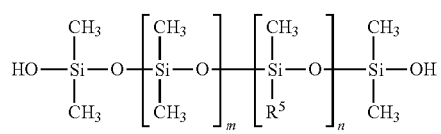

(4)

(in the chemical formula (4), $-R^5$ is the same as above; m is a number of 1-1500; n is a number of 5-100).

In the sliding member, the coating layer composition contains an alkali ingredient.

In the sliding member, for example, the alkali ingredient is sodium hydrogen carbonate and/or sodium carbonate.

In the sliding member, a rubber ingredient exposed on a surface of the elastic molded body is bonded to the amino-modified silicone compound in the coating layer composition.

In the sliding member, at least any molecules of the amino-modified silicone compound may react each other, and/or a functional group on a surface of the elastic molded body and a molecule of the amino-modified silicone compound may react each other, through the silanol group and/or the alkoxysilyl group.

A method for manufacturing a sliding member to achieve the objects according to the patent claims comprises the following steps:
    preparing a coating layer composition containing an amino-modified silicone compound having a silanol group and/or an alkoxysilyl group and also having an amino-containing group in a side chain;
    applying the coating layer composition to an elastic molded body; and
    coating the elastic molded body with the coating layer composition.

It is more preferable that the method for manufacturing the sliding member contains further adding an alkali ingredient into the coating layer composition.

Effects of the Invention

The sliding member of the present invention possesses a significantly low sliding resistance property compared with the previous one and, in addition, exhibits excellent slidable ability. The sliding member exhibits high liquid-sealing properties due to the excellent physical property of the elastic molded body made of the rubber component with sufficient elasticity such as a butyl rubber, a halogenated butyl rubber, or the like, and hence does not cause leaking.

The sliding member is useful as a sliding member for various applications such as a gasket for medical syringes or injectors, packing and O-rings that require sufficient slidability and liquid-sealing ability without affecting basic properties such as a low permanent compression set inherent in the elastic molded body made of the rubber component such as a butyl rubber, a halogenated butyl rubber, or the like.

The sliding member has low dust emission and low leachability properties, because the amino-modified silicone compounds react on the surface of the elastic molded body to form bonds. Accordingly, it can improve safety and reliability, and hence it is suitable for treatment and diagnostic testing.

The sliding member can fulfill the standard set at The Japanese Pharmacopoeia such as the standard test for the rubber plug testing method for fluid infusion. And based on the facts that eluates to contact liquids such as water or medical solution are extremely low and the generation of chlorides as the set for a water purity test is suppressed, thereby the sliding member can be used as the gasket for medical syringes or injectors.

According to the method for manufacturing the sliding member of the present invention, the sliding member having the characteristics can be manufactured simply by handy operation in high quality with high volume and good yield.

According to the method, it can contribute to the reduction of manufacturing and medical expenses, since it is possible to manufacture from inexpensive raw materials.

BRIEF DESCRIPTION OF DRAWINGS

FIG. 1 This represents a correlation between the moving distance and the sliding resistance value with the sliding member shown by Examples of the present invention and the sliding member shown by Comparative Examples not applicable the present invention.

EMBODIMENTS TO IMPLEMENT THE INVENTION

The following details the favorable embodiments for implementing the present invention, but the scope of the present invention is not limited to these embodiments.

A sliding member of the present invention comprises an elastic molded body coated with a coating layer composition containing an amino-modified silicone compound having a silanol group and/or an alkoxysilyl group in the middle and/or the terminal, favorably at the either terminal or terminal, and more favorably at the both terminals of the main chain thereof, and an amino-containing group in the side-chain extending from the main chain.

As materials of the elastic molded body in the sliding member, the rubber component is selected from the groups consisting of a butyl rubber such as a copolymer rubber of isobutylene and isoprene; a halogenated butyl rubber selected from the group consisting of a chlorinated butyl rubber, a brominated butyl rubber, and a polychloroprene rubber, a copolymer of chlorinated isobutylene and isoprene, a copolymer of brominated isobutylene and isoprene, and a bromine-added polymer of copolymer of isobutylene and p-methylstyrene. These rubber components can be used as a raw material of the slidable elastic molded body, in particular, the slidable elastic molded body for medical use that needs to reduce the permanent compression set. The elastic molded body may contain a filler, a vulcanization agent and a vulcanizing auxiliary agent.

The coating layer covering the elastic mold body, in which the amino-modified silicone compounds are contained and/or are reacted and crosslinked in a part thereof with the rubber component such as a halogenated butyl rubber of the elastic molded body, is bonded to a surface of the sliding member through strong bonding by reacting with molecules of the amino-modified silicone compounds onto the sliding member, due to substitution reaction of an amino group of the amino-modified silicone and a halogen atom of the rubber component exposed on a surface of the sliding member such as the butyl rubber and halogenated butyl rubber, especially the halogenated butyl rubber. These coating layers may be a single-molecule layer arranged with many molecules of the amino-modified silicone compounds or may be a layer where many molecules of the amino-modified silicone compounds bind or are cured.

Furthermore, in the sliding member, silanol groups and/or alkoxysilyl groups of amino-modified silicone compounds that bind to the surface functional groups of an elastic molded body and react, otherwise silanol groups and/or alkoxysilyl groups of reacted amino-modified silicone compound molecules and unreacted amino-modified silicone compound molecules may react each other by ether coupling through dehydration or dealcohol, and it may also react in a retinal manner.

The amino-modified silicone compounds that form the coating layer may be an amino-modified silicone oil introduced with an amino-group as an organic substituent. For example, this may be an amino-modified silicone oil with an amino-group on any one of the silicone repetitive units and/or at the terminal or the amino-modified silicone oil with an amino-group on one of the silicone repetitive units and/or at the terminal plus a hydroxyl- or protected hydroxyl-group on any one of the silicone repetitive units and/or at the terminal. Such an amino-substituent group may be an amino-group, an aminoalkyl-group such as an aminopropyl-group, an N-(β-aminoalkyl)iminoalkyl group such as an N-(β-aminoethyl)iminopropyl group and, of course, a composite group in which several of them are connected sequentially. In addition, such an amino-group may be a mono-amino-substitution or a polyamino-substitution such as a diamino-substitution, and also an alkyl group of them may be replaced with a hydroxyl group and/or an alkoxysilyl group.

In the coating layer composition, the amino-modified silicone compound has siloxane-repeating units which are presented with the following chemical formula (1)

[Chemical expression 5]

(1)

(in the chemical formula (1), -$R^2$ and -$R^3$ are independently a saturated or an unsaturated alkyl group having 1-3 carbons, for example, a methyl group, an ethyl group, an n-propyl group, an isopropyl group, a vinyl group, or an allyl group; or a phenyl group); siloxane-repeating units having the amino-containing group, wherein an alkyl group having a primary, secondary or tertiary amino is present, which are presented with the following chemical formula (2)

[Chemical expression 6]

(2)

(in the chemical formula (2), -$R^4$ is a saturated or an unsaturated alkyl group having 1-3 carbons, for example, a methyl group, an ethyl group, an n-propyl group, an isopropyl group, a vinyl group, or an allyl group; or a phenyl group. -$R^5$ is -$U^1$-N(—$R^a$)-$V^1$-N(—$R^b$)-$W^1$-NH(—$R^c$), -$U^2$-N(—$R^d$)-$V^2$-NH(—$R^e$) or -$U^3$—NH(—$R^f$) (providing that -$U^1$-, -$U^2$-, -$U^3$-, -$V^1$-, -$V^2$-, and -$W^1$- are —$(CH_2)_x$— (providing that x is a number of 2-4), or —$(CH_2)_{y1}$—(CH(CH_3))_{y2}—(CH_2)_{y3}$— (providing that y1 and y2 are a number of 0-4, y3 is a number of 1-4); -$R^a$, -$R^b$, -$R^c$, -$R^d$, -$R^e$, and -$R^f$ are independently a hydrogen atom, —$(CH_2)_z$—$CH_3$ (providing that z is a number of 0-3), or —$(CH_2CH(OH)CH_2(OH))$); and silanol units having a silanol group and/or an alkoxysilyl group which are presented with the following chemical formula (3):

[Chemical expression 7]

(3)

(in the chemical formula (3), -$R^1$ is a hydrogen group, a methyl group, an ethyl group, or an n-propyl group. -$R^6$ is a saturated or an unsaturated alkyl group having 1-3 carbons, for example, a methyl group, an ethyl group, an n-propyl group, an isopropyl group, a vinyl group, or an allyl group; or a phenyl group. -$R^7$ is a saturated or an unsaturated alkyl group having 1-3 carbons for example, a methyl group, an ethyl group, an n-propyl group, an isopropyl group, a vinyl group, or an allyl group if silanol groups and/or alkoxysilyl groups are at the terminal of the main chain thereof; or a phenyl group; a binding moiety to the adjacent unit if silanol groups and/or alkoxysilyl groups are in the middle of the side chain).

The amino-modified silicone compound may be more preferably a compound which is presented with the following chemical formula (4):

[Chemical expression 8]

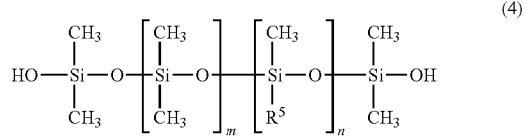

(4)

(in the chemical formula (4), -$R^5$ is the same as above; m is a number of 1-1500, and more favorably a number of 5-100; n is a number of 5-100. The dimethylsiloxy units having m and the (methyl group-substituted) (amino-containing group-substituted) siloxy units can be block co-polymerized or random co-polymerized, and, of course, some can be block co-polymerized and some other parts can be random co-polymerized).

The amino-modified silicone oil may be, specifically, BY16-879B (viscosity 1500 mm²/s [25° C.], functional group equivalent 7500) and BY16-892 (viscosity 1400 mm²/s [25° C.], functional group equivalent 1900) (all trade names, available from Dow-Toray Co., Ltd.); KF-857 (viscosity 65 mm²/s [25° C.], functional group equivalent 790), KF-8001 (viscosity 240 mm²/s [25° C.], functional group equivalent 1900), and KF-862 (viscosity 650 mm²/s [25° C.], functional group equivalent 1900) (all trade names, available from Shin-Etsu Chemical Co., Ltd.); TSF4703 (viscosity 1000 mPa·s [25° C.], functional group equivalent 1600), TSF4704 (viscosity 40000 mPa·s [25° C.], functional group equivalent 20000), TSF4705 (viscosity 70000 mPa·s [25° C.], functional group equivalent 40000), TSF4707 (viscosity 10000 mPa·s [25° C.], functional group equivalent 7000), TSF4708 (viscosity 1000 mPa·s [25° C.], functional group equivalent 2800), and XF42-B1989 (viscosity 900 mPa·s [25° C.], functional group equivalent 0.9 Nwt %) (all trade names, available from Momentive Performance Materials Japan LLC).

In the coating layer composition, the concentration of the amino-modified silicone compound is not particularly limited, but, specifically, the emulsion has favorably 0.0002-0.5 mass %, and more favorably 0.01-0.3 mass %.

The coating layer composition contains preferably an alkali ingredient. The alkali ingredient may be sodium hydrogen carbonate and/or sodium carbonate. The presence of the alkali ingredient in the coating layer composition makes it easier for the amino-modified silicone compound to react with the rubber component such as a butyl rubber and a halogenated butyl rubber. As a result, it can be estimated that the number of the amino-modified silicone molecule per unit area bound to the surface functional group of the elastic molded body can be increased, the sliding resistance value can be lowered, and hence slidability can be improved. If the coating layer composition does not contain the alkali ingredient, the sliding resistance value of the sliding member should be 9N or more, for example, around 9-10N. But when the coating layer composition does contain the alkali ingredient, the sliding resistance value of the sliding member should be reduced to 6-8N, for example, around 6-7N.

The coating layer composition may contain the amino-modified silicone compounds and, if necessary, the alkali ingredient plus media, for example, solvent or dispersion medium, specifically water, for dissolution or dispersion. The coating layer composition can be either a solution or emulsion.

The coating layer composition may contain surfactants. The surfactants include anionic surfactants such as an alkylsulfonic acid salt, alkylbenzenesulfonic acid salt, alkylphosphonic acid salt, or the like; non-ionic surfactants such as a polyoxyalkylene alkyl ether, polyoxyethylene alkylphenyl ether, polyoxyethylene aliphatic acid ester, sorbitan aliphatic acid ester, or the like; cationic surfactants such as a quaternary ammonium salt, alkylamine acetic acid salt, or the like; amphoteric surfactants such as an alkylbetaine, alkylimidazoline, or the like. The emulsion containing the amino-modified silicone compounds may contain dissolving agents, for example, ethers such as a polyoxyethylene branched alkyl (C12-C14) ether, siloxanes such as octamethylcyclotetrasiloxane, and organic acids such as acetic acid.

The coating layer can be prepared by immersing the optionally-cleaned elastic molded body to the coating layer composition consisting of an emulsion containing the amino-modified silicone compounds, water rinsing and drying as appropriate. In this case, an amino-substituent or a hydroxyl-group of the amino-modified silicone compound reacts with a halogen-group of the rubber components such as the halogenated butyl rubber of the elastic molded body and, if fillers such as silica or talc are coexisted, it reacts with their surface hydroxyl-groups to form covalent bonds and membrane-like coating layers.

The presence of this coating layer leads to the reduction of the dynamic sliding resistance value of the sliding member to around 9-10N. For example, when a gasket ($\varphi$=ca. 20.8 mm) with the same profile as its inner diameter slides into a PP resin outer tube for 20 mL, the dynamic sliding resistance value under 1 mm/min can be suppressed to 10N or less.

The elastic molded body may contain a filler, a vulcanization agent or a vulcanizing auxiliary agent.

The filler may be granules or a powder and includes the followings: inorganic filler such as talc; silica obtained, for example, by a precipitation method; titanium oxide as a rutile-type or an anatase-type, and titanium oxide manufactured by a chlorine method or a sulfuric acid method; carbon black; clay; calcium carbonate; or an organic filler such as polymer fine particles, for example, a powder filler of ultra-high molecular weight polyethylene (UHMW-PE) with an average molecular weight such as a viscosity average molecular weight being between 1 million and 4 million. These fillers may be a packing agent designed to improve the mechanical strength and color. These fillers can be used alone or with multiple mixes.

These fillers can be treated with an alkoxysilane compound on their surfaces. This alkoxysilane compound may be a silane coupling agent, for example, an alkoxysilane compound that may be further contained in the elastic molded body composition.

In the elastic molded body, the filler content is favorably 10-150 parts by mass for the 100 portions by mass of the rubber component, and more favorably 20-150 parts by mass.

The vulcanization agent may be a nitrogen- or sulfur-containing compound. The vulcanization agent is used to vulcanize the elastic molded body composition containing the rubber component, filler and vulcanization agent to form the elastic molded body.

As the vulcanization agent, for example, a nitrogen- or sulfur-containing compound may be triazinethiol derivatives and 2-mercaptobenzimidazole derivatives. Specifically, this may be the triazinethiol derivatives as presented with the following chemical formula (5):

[Chemical expression 9]

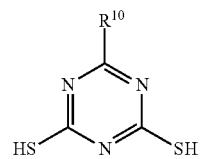

(5)

(in the chemical formula (5), $R^{10}$ denotes —SH, —$OR^{11}$, —$SR^{12}$, —$NHR^{13}$, or —$NR^{14}R^{15}$ ($R^{11}$-$R^{15}$ may be identical or different respectively, and may be an alkyl group, alkenyl group, allyl group, aralkyl group, alkylallyl group, or cycloalkyl group. $R^{14}$ and $R^{15}$ may be identical or different. $R^{11}$-$R^{15}$, for example, may be linear, branched, and/or cyclic with a maximum of 20 carbon atoms));
the 2-mercaptobenzimidazole derivatives as presented with the following chemical formula (6):

[Chemical expression 10]

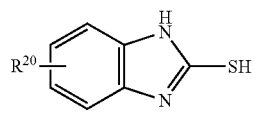

(6)

(in the Formula (6), $R^{20}$ denotes a hydrogen or methyl group).

As the vulcanization agent, the triazinedithiol derivatives may be specifically 2-dibutylamino-4,6-dimercapto-s-triazine, 2-anilino-4,6-dimercapto-s-triazine, and 2,4,6-trimercapto-s-triazine. In the elastic molded body, the content of the triazinedithiol derivatives is favorably 0.5-2.0 parts by mass for the 100 portions by mass of the rubber component, and more favorably 0.5-1.5 parts by mass. When the content of the triazinedithiol derivatives was less than 0.5 parts by mass, sufficient vulcanization cannot be obtained.

As the vulcanization agent, the 2-mercaptobenzimidazole derivatives may be, more specifically, 2-mercaptobenzimidazole and 2-mercapto-5-methylbenzimidazole. In the elastic molded body, the content of the 2-mercaptobenzimidazole derivatives is favorably 0.5-1.5 parts by mass for the 100 portions by mass of the rubber component.

The vulcanization auxiliary agent may be a zinc compound. The vulcanization auxiliary agent can regulate the time until the vulcanization reaction starts and the reaction rate of vulcanization, and thereby the vulcanization reaction can be controlled.

As the vulcanization auxiliary agent, the zinc compound may be an organic acid zinc salt. For example, the organic acid zinc salt may be a zinc salt of saturated or unsaturated aliphatic acids with 10-24 carbon atoms, or of aromatic carboxylic acids, specifically, a stearic acid zinc salt, behenic acid zinc salt and montanic acid zinc salt. The organic acid zinc salts can regulate the time until the vulcanization reaction starts and the reaction rate of vulcanization, and thereby the vulcanization reaction can be controlled, when the elastic molded body composition is vulcanized. In the elastic molded body, the content of the organic acid zinc salt is less than 0.5 parts by mass for the 100 portions by mass of the rubber component. But in order to control the vulcanization reaction, its content is favorably 0.1 parts by mass or more and less than 0.5 parts by mass, and more favorably 0.2-0.3 parts by mass. Even if the content of the organic acid zinc salt is 0.5 parts by mass or more, the effect of extending the start time of the vulcanization reaction in proportion to the amount of the additive is not achieved, and, moreover, it is not desirable because the amount of zinc elution increases as well.

In the sliding member, the elastic molded body may contain optionally the components plus additives, if necessary. The additives may be an acid-acceptor such as magnesium oxide, zinc oxide and natural or synthetic hydrotalcite; an anti-adhesion and viscosity regulator such as stearic acid, or the like; and a processing auxiliary agent such as a softener like a silicone oil and paraffin oil. As the acid-acceptor, in order to prevent the elution of zinc and the generation of chlorides, it is preferable to use magnesium oxide with a BET-specific surface area of 30-165 m²/g, which can be determined by a BET (Brunauer-Emmett-Teller) method. Among these, by blending with medium active magnesium oxide with the BET-specific surface area of 30-40 m²/g, the highly productive vulcanization reaction with long start time and short time to reach equilibrium vulcanization can be achieved, while the eluate and the permanent compression set remain low.

Furthermore, the elastic molded body composition may contain alkoxysilane compounds. These alkoxysilane compounds, for example, can act as a silane coupling agent. These alkoxysilane compounds may be alkoxysilane compounds having mercapto-groups, mercapto-producing functional groups, amino groups and/or amino-producing functional groups. The mercapto-producing group and amino-producing functional group mean the groups that can produce a SH-group and $NH_2$-group, respectively, by reduction or deblocking.

One example of the alkoxysilane compounds may have an alkoxy group, but also have a mercapto-group and/or mercapto-producing group. The mercapto-producing functional group means a group that can produce an SH-forming group by reduction or deblocking. For example, although bis(3-(triethoxysilyl)propyl)tetrasulfide (TESPT) does not contain an SH group within its original structure, it can generate an —S—SH group or —SH group by disconnection of some bonds in the middle of the chain of four sulfur atoms connected together (—S—S—S—S—) during vulcanization. Specifically, this may be the polysulfide group (—(S)$_p$—, p=2-4) such as a disulfide function (—S—S—) and the protected mercapto-group with a methyl or trimethylsilyl protective group.

The alkoxysilane compounds may be an alkoxysilane compound containing alkoxy- and mercapto-groups, typically, 3-mercaptopropyltrimethoxysilane and 3-mercaptopropylmethyldimethoxysilane; an alkoxysilane compound containing alkoxy- and mercapto-producing functional groups, typically, an alkoxysilane compound containing a polysulfide function such as bis(3-(triethoxysilyl)propyl) tetrasulfide or a block body of alkoxysilane compounds containing a mercapto function. Among these, 3-mercaptopropyltrimethoxysilane is recommended. These alkoxysilane compounds can be used alone or with multiple mixes.

Another example of the alkoxysilane compounds is an alkoxysilane compound with alkoxy groups but with additional amino groups and/or amino-producing functional groups. For example, this may be the alkoxysilane compounds having an amino group or its block body. The amino-producing compound, for example, means a protected amino group, for example, a protected amino group having a carbamate-type protective group such as a tert-butoxycarbonyl or benzyloxycarbonyl group; a protected amino group having an amide-type protective group; a protected amino group having an imide-type protective group such as a phthaloyl group; a protected amino group having a sulfonamide-type protective group such as a p-toluenesulfonyl group or 2-nitrobenzenesulfonyl group.

The alkoxysilane compounds may be an alkoxysilane compound having an alkoxy group and an amino group, for example, 3-aminopropyltrimethoxysilane, 3-aminopropyltriethoxysilane, N-2-(aminoethyl)-3-aminopropylmethyldimethoxysilane and N-2-(aminoethyl)-3-aminopropyltrimethoxysilane. Among these, 3-aminopropyltrimethoxysilane is recommended. These alkoxysilane compounds can be used alone or with multiple mixes.

The content of the alkoxysilane compound is favorably 0.2-2.0 mass % for the filler mass portion, and more favorably 0.5-2.0 mass % in the blend of the elastic molded body composition.

These alkoxysilane compounds are connected with the filler surface by blending with the elastic molded body composition and/or providing the surface treatment of the filler, and the filler and polymers are bonded together via the alkoxysilane compounds thereof. In the elastic molded body, the filler can connect with the main chain of the polymer by making bonds with the rubber components such as a halogenated rubber via the alkoxysilane compounds thereof, in forming a three-dimensional mesh structure.

Specifically, this is a substance in which the reactive functional groups such as a hydroxyl group on the filler surface react with an alkoxy group as an hydrolyzing group in alkoxysilane compounds to form bonds, and further an amino-group or amino-producing group of those alkoxysilane compounds or a mercapto-group or a mercapto-producing group such as a disulfide group reacts with a halogen atom of the halogenated rubber to form bonds. The bond between the alkoxysilane compounds and the filler may be spread out over several parts on the filler surface, and the filler surface may be bonded to coat with the alkoxysilane compounds.

In the elastic molded body, the filler connects with the polymer chain via the alkoxysilane compounds. Due to the hydrophobic property of the filler surface connected with the alkoxysilane compounds, it is difficult for permanganate reductants to be extracted to the contact fluid side even during elution tests in the rubber plug testing method for fluids at The Japanese Pharmacopoeia. Furthermore, it is favorable that these fillers are treated with alkoxysilane compounds on their surface, and hence the permanent compression set can be reduced significantly because of no misalignment of the interface with the halogenated rubber.

Accordingly, the alkoxysilane compounds are contained with the fillers in forming chemical bonds on their filler surface, and can prevent misalignment of the interface as one of the causes of permanent compression set between the filler and the polymer formed by a halogenated rubber, and this leads to the considerable reduction of the permanent compression set. In addition, the alkoxysilane compounds can prevent the elution of metal chlorides such as magnesium chloride or zinc chloride formed from metal oxides such as magnesium oxide or zinc oxide in the elastic molded body composition from the elastic molded body.

The sliding member of the present invention is manufactured as follows.

First of all, the sliding member-forming composition containing at least any one of the rubber components selected from a butyl rubber and halogenated butyl rubber, a filler, a vulcanization agent, and optionally, an additive such as alkoxysilane compounds as silane coupling agents, an acid acceptor, a colorant, and/or a processing auxiliary agent including an anti-adhesion and viscosity regulator or softeners, are all kneaded with open rolls, or the like.

By the way, to prepare the sliding member-forming composition, an integral blend method in which all ingredients are formulated together can also be used. Alternatively, as a preparative method, after the preparation of surface-treated fillers by reacting first fillers with alkoxysilane compounds as a pre-treatment process, the addition of those surface-treated fillers to each of the remaining component followed by kneading can also be used.

As a direct surface treatment method for the fillers using alkoxysilane compounds in advance, after stirring an aqueous solution of silane coupling agents, that is, alkoxysilane compounds, with a powdered filler, heating and drying to cause the reaction can be used. Through the reaction of reactive functional group such as a hydroxyl group on the filler surface with the alkoxy group of the alkoxysilane compounds to bind, the alkoxysilane compounds can be set on the filler surface.

Whether it is the elastic molded body composition mixed and blended with all ingredients at once or the other elastic molded body composition using the fillers pre-treated on their surface with alkoxysilane compounds, the alkoxysilane compounds are chemically bonded to the filler surface by being vulcanized and molded similarly as above, and thus the elastic molded body in which the filler is bonded to the halogenated rubber via the alkoxysilane compounds can be obtained.

Next, to the cavity of a vulcanization mold such as a dual-piece-type vulcanization mold having a male-type with a protrusion that forms a plunger hole and a female-type machined to form a cone is filled an appropriate amount of the kneaded rubber part-forming composition, and then this is subjected to heat-pressing and decoration at 165-190° C. and at 15-20 atmospheric pressure for 7-20 min., favorably 7-15 min., to be molded into a sheet. A number of gasket-shaped sheets formed in a variety of forms into sheets are subjected to vent-pressing, and then cut into the desired gasket-shaped individual piece by using a pulling mold. This gasket-shaped piece is rinsed, if necessary. This rinsing process relies on rinsing by water and/or alkaline rinsing with aqueous sodium carbonate solution and/or subsequent acid-rinsing with aqueous sulfuric acid solution. This gasket piece is dried, if necessary.

The hardness of the gasket-shaped piece obtained above is favorably a Duro A hardness of 40 as lower-limit, more favorably 50, and is favorably a Duro A hardness of 75 as upper-limit, more favorably 70, much more favorably 65, most favorably 60 (JIS K 6253-3:2012 Duro A).

To the emulsion of the coating layer-forming composition containing amino-modified silicone compounds and alkali ingredients are immersed the pieces of gasket shape, and then the composition is applied to those pieces, water-rinsed, if necessary, and dried naturally or air-dried, if necessary. Otherwise when the coating layer is formed by heating up at room temperature-120° C. for 30 min-3 h, the medical gasket can be obtained as a sliding member.

When the end of the plunger is pushed into the plunger hole of the gasket, and then the plunger with the gasket is inserted into a syringe barrel or injector barrel, a syringe or injector can be formed. The syringe may be the pre-filled syringe.

EMBODIMENTS

The following is a detailed explanation of examples of the implementation of the present invention for medical gaskets made of sliding members.
(Examples of Elastic Molded Body Preparation)
At first, the rubber formulation for elastic molded body preparation was prepared.
After stirring and mixing 100.00 parts by mass of chlorinated butyl rubber (JSR CHLOROBUTYL 1066: trade name, available from JSR Corporation) as a polymer component, 0.30 parts by mass of stearic acid (purified stearic acid 550V: trade name, available from KAO co., Ltd.), 0.30 parts by mass of zinc stearate (Zn-St (plant): trade name, available from NITTO Chemical Industry Co., Ltd.), and 5.00 parts by mass of paraffinic oil (DYANA PROCESS OIL PW-380: trade name, available from IDEMITSU KOSAN Co., Ltd.) as processing aid agents, 2.00 parts by mass of magnesium oxide (Kyowa Magu #30: trade name, available from Kyowa Chemical Industry Co., Ltd.) as an acid-acceptor, 0.30 parts by mass of carbon black (Asahi #35: trade name, available from Asahi Carbon Co., Ltd.) and 3.00 parts by mass of sulfuric acid method rutile-type titanium oxide (TIPAQUE R-630: trade name, available from Ishihara Sangyo Kaisha, Ltd.) as colorants, 60.00 mass % of talc (GH3: trade name, available from Hayashi Kasei Co., Ltd.) and 20.00 mass % of ultra-high molecular weight polyethylene (MIPELON XM-220: trade name, available from Mitsui Chemicals Inc.) as fillers, and 0.60 mass % of 3-mercaptopropyltrimethoxysilane (DOWSIL Z-6062 Silane: trade name, available from Dow-Toray Co., Ltd.) as an alkoxysilane compound with a sealed pressure kneader, to this kneaded mixture was added 0.70 parts by mass of 6-(dibutylamino)-1,3,5-triazine-2,4-dithiol (ZISNET DB: trade name, available from Sankyo Kasei Co., Ltd.) as a vulcanization agent and stirred and mixed with an open roll to obtain the rubber formulation for the elastic molded body preparation.

The rubber formulation was cut properly in an automatic machine to fill into a cavity of a vulcanization mold with an appropriate weight and shape, and thus the rubber raw material was pre-molded. This pre-molded rubber raw material was put into a gasket shape-forming mold followed by press-heating in a vulcanization-molding press-machine at 180° C. for 10 min, and, after vulcanization and molding into a gasket shape, the rubber sheet for gaskets was obtained.

A number of the gasket-shapes formed in the form of sheets were cut into an appropriate-shaped piece using punching-press with a punching die to afford the elastic molded body as a rubber part for gaskets.

The elastic molded body was immersed in 0.6 weight % of an aqueous sodium carbonate solution, boiled for 90 min, and finally immersed again in 1.9 weight % of an aqueous sulfuric acid solution at room temperature for 120 min as a chemically cleaning treatment to afford the chemically cleaned elastic molded body.

Example 1

An emulsion solution as a coating layer-forming composition was prepared by mixing 25.0 g of an amino-modified silicone oil bearing a terminal hydroxyl group (DOWSIL BY16-892: trade name, available from Dow-Toray Co., Ltd.), 2.7 g of a surfactant (NIKKOL BT-9: trade name, available from NIKKO Chemicals Co., Ltd.), 1.0 g of octamethylcyclotetrasiloxane (TSF-404: trade name, available from Momentive Performance Materials Japan LLC), and 71.3 g of 0.5 weight % of an aqueous acetic acid solution followed by stirring for 10 min at 8000 rotation/min with a homo-mixer.

By using the prepared emulsion solution, an aqueous solution for immersion was prepared by mixing with ion-exchange water to obtain a concentration of 0.05 weight % of the silicone oil component.

The chemically cleaned elastic molded body was immersed in the aqueous solution for immersion at 40° C. for 30 min. Thereafter the elastic molded body was taken out of the liquid and, after 1-min rinsing three times, drying with air blow to form the coating layer so as to cover the elastic molded body, and thus the desired medical gasket was obtained as sliding members.

Example 2

An emulsion solution as a coating layer-forming composition was prepared by mixing 25.0 g of an amino-modified silicone oil having a terminal methoxy group (KF-862: trade name, available from Shin-Etsu Chemical Co., Ltd.), 2.7 g of a surfactant (NIKKOL BT-9: trade name, available from NIKKO Chemicals Co., Ltd.), 1.0 g of octamethylcyclotetrasiloxane (TSF-404: trade name, available from Momentive Performance Materials Japan LLC), and 71.3 g of 0.5 weight % of an aqueous acetic acid solution followed by stirring for 10 min at 8000 rotation/min with a homo-mixer, and thus, similar to Example 1, the medical gasket was obtained as sliding members.

Example 3

By using the emulsion solution prepared in the same manner as in Example 1, an aqueous solution for immersion was prepared by mixing with ion-exchange water to obtain a concentration of 0.05 weight % of the silicone oil component and a concentration of 0.01 weight % of sodium hydrogen carbonate, and thus, similar to Example 1, the medical gasket was obtained as sliding members.

Example 4

By using the emulsion solution prepared in the same manner as in Example 2, an aqueous solution for immersion was prepared by mixing with ion-exchange water to obtain a concentration of 0.05 weight % of the silicone oil component and a concentration of 0.01 weight % of sodium hydrogen carbonate, and thus, similar to Example 1, the medical gasket was obtained as sliding members.

Comparative Example 1

Without coating treatment of the chemically cleaned elastic molded body the medical gasket was obtained as sliding members.

Comparative Example 2

A solution as a coating layer-forming composition was prepared by mixing 25.0 g of a polyether-type silicone oil (KM-244F: trade name, available from Shin-Etsu Chemical Co., Ltd.) and 75.0 g of ion-exchange water followed by stirring for 10 min at 8000 rotation/min with a homo-mixer, and thus, in the same manner as in Example 1, the medical gasket was obtained as sliding members.

Comparative Example 3

By using the emulsion solution containing a dimethylsilicone oil (KM-742T: trade name, available from Shin-Etsu Chemical Co., Ltd.) as an emulsion solution, in the same manner as in Example 1, the medical gasket was obtained as sliding members.

Comparative Example 4

By using the emulsion solution containing an amino-modified silicone oil having a terminal methyl group (PO-LON-MF14: trade name, available from Shin-Etsu Chemical Co., Ltd.) as an emulsion solution, in the same manner as in Example 1, the medical gasket was obtained as sliding members.

(Physical Properties Evaluation Test 1: Sliding Resistance Measurement Test)

For the sliding members obtained in Examples 1-4 and Comparative examples 1-4, each three samples of a ready-made gasket at the tip of a plunger of a commercially available syringe (available from Terumo Corporation) with an outer barrel for a syringe with a length of 93 mm and an inner diameter of 19.7 mm were replaced with the gasket prepared above, a silicone oil (SH200 50 cs: available from Dow-Toray Co., Ltd.) was applied to the inner wall of an outer barrel for a syringe, and the plunger was inserted to the required mark on the outer barrel. Thereafter the measurement of the load at the time when the plunger was pushed in it at a speed of 1 mm/min. from a given surface was performed by using an instrument of a digital force gauge (HF-100: trade name, available from Japan Instrumentation System Co., Ltd.). The maximum load at that time was measured as a sliding resistance, and the results are shown in Table 1 and FIG. 1.

(Physical Properties Evaluation Test 2: Pulsation Test)

From the results of FIG. 1, the pulsation was confirmed by the presence or absence of graph variation during the sliding motion. The results are shown in Table 1.

(Physical Properties Evaluation Test 3: External Appearance Observation Test)

For the sliding members obtained in Examples 1-4 and Comparative examples 1-4, the external appearance was observed. The results are summarized in Table 1.

TABLE 1

|  |  | Ex. 1 | Ex. 2 | Ex. 3 | Ex. 4 | Comp. Ex. 1 | Comp. Ex. 2 | Comp. Ex. 3 | Comp. Ex. 4 |
| --- | --- | --- | --- | --- | --- | --- | --- | --- | --- |
| Sliding | n = 1 | 9.0 | 9.0 | 6.8 | 7.2 | ND | 22.4 | 26.1 | 35.5 |
| Resistance | n = 2 | 10.4 | 9.7 | 7.2 | 8.3 | ND | 22.6 | 26.6 | 38.2 |
| Value | n = 3 | 8.7 | 8.4 | 6.5 | 5.8 | ND | 22.3 | 25.8 | 31.5 |
| (N) | Average | 9.6 | 9.0 | 6.8 | 7.1 | ND | 22.4 | 26.2 | 35.1 |
| Pulsation |  | No | No | No | No | Yes | No | No | No |
| External Appearance |  | Gloss Black-color Homogeneous | Gloss Black color Homogeneous | Gloss Black-color Homogeneous | Gloss Black-color Homogeneous | Gloss Black-color Homogeneous | Gloss Black-color Uneven | Black-color Spotted Pattern | Gloss Black-color Homogeneous |

As clearly shown in Table 1 and FIG. 1, the sliding members shown in the examples of the implementation of the present invention were very low with a sliding resistance value of 10N or less, and in addition the coating layer was well-formed homogeneously. Furthermore, as shown in examples 3 and 4 in which alkaline ingredients were involved, the sliding resistance value was considerably reduced, resulting in a high effect. In contrast, for the sliding member shown by comparative examples not applicable the present invention, the correct sliding resistance value could not be measured, because, as shown in comparative example 1, the graph variation during sliding occurred, causing pulsation. In comparative examples 2-4, sufficient sliding abilities could not be obtained, because the sliding resistance value was very high at 22N or more and, in addition, the coating layer was uneven and spotted.

INDUSTRIAL APPLICABILITY

The sliding member of the present invention can be used as follows: syringes that inject a liquid medicine into patients after inhaled it and then pushed it out, pre-filled syringes that inject a pre-sealed liquid medicine into patients by pushing it out when used or into an infusion solution when used, and gaskets for blood drawing. In addition, this can also be used as a variety of rubber parts including a slidable packing, O-rings, or the like.

The method for manufacturing the sliding member of the present invention is useful for producing the high quality sliding member, since the method is simple to operate using inexpensive raw materials and easy to mass-produce with good yields.

What is claimed is:
1. A sliding member comprising:
an elastic molded body which is coated with a coating layer composition containing an amino-modified silicone compound having a silanol group and/or an alkoxysilyl group and also having an amino-containing group in a side chain,
wherein the amino-modified silicone compound has:
siloxane-repeating units represented by the following chemical formula (1)

wherein in the chemical formula (1), $-R^2$ and $-R^3$ are independently an alkyl group having 1-3 carbons or a phenyl group;
siloxane-repeating units having the amino-containing group and which are represented by the following chemical formula (2)

wherein in the chemical formula (2),
$R^4$ is an alkyl group having 1-3 carbons or a phenyl group; and
$R^5$ is $-U^1-N(-R^a)-V^1-N(-R^b)-W^1-NH(-R^c)$, or $-U^2-N(-R^d)-V^2-NH(-R^e)$, wherein -U¹-, -U²-, V¹-, -V²- and -W¹- are —(CH₂)ₓ—, where x is a number of 2-4, or —(CH₂)ᵧ₁—(CH(CH₃))ᵧ₂—(CH₂)ᵧ₃—, where y1 and y2 are a number of 0-4 and y3 is a number of 1-4, and -Rᵃ, -Rᵇ, -Rᶜ, -Rᵈ, and -Rᵉ are independently a hydrogen atom, —(CH₂)_z—CH₃, where z is a number of 0-3, or —(CH₂CH(OH)CH₂(OH)); and silanol units having the silanol group and/or alkoxysilyl group and which are represented by the following chemical formula (3)

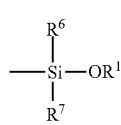

(3)

wherein in the chemical formula (3),
R¹ is a hydrogen group, a methyl group, an ethyl group, or a n-propyl group;
R⁶ is an alkyl group having 1-3 carbons, or a phenyl group; and
R⁷ is an alkyl group having 1-3 carbons, a phenyl group, or a binding moiety.

2. The sliding member according to claim 1, wherein the elastic molded body is an elastic molded body including at least one of a rubber ingredient selected from the group consisting of butyl rubber and halogenated butyl rubber.

3. The sliding member according to claim 1, wherein the amino-modified silicone compound has the silanol group and/or the alkoxysilyl group at one terminal or both terminal of a main chain thereof.

4. The sliding member according to claim 3, wherein the amino-modified silicone compound is represented by the following chemical formula (4)

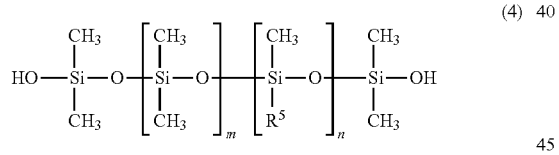

(4)

wherein in the chemical formula (4), -R⁵ is the same above; m is a number of 1-1500; and n is a number of 5-100.

5. The sliding member according to claim 1, wherein the coating layer composition further includes an alkali ingredient.

6. The sliding member according to claim 5, wherein the alkali ingredient is sodium hydrogen carbonate and/or sodium carbonate.

7. The sliding member according to claim 1, wherein a rubber ingredient exposed on a surface of the elastic molded body is bonded to the amino-modified silicone compound in the coating layer composition.

8. The sliding member according to claim 1, wherein at least any molecules of the amino-modified silicone compound react with each other, and/or a functional group on a surface of the elastic molded body and a molecule of the amino-modified silicone compound react, through the silanol group and/or the alkoxysilyl group.

9. The sliding member according to claim 1, wherein R¹ is a methyl group, an ethyl group, or an n-propyl group.

10. A method for manufacturing a sliding member comprising steps of:
preparing a coating layer composition containing an amino-modified silicone compound having a silanol group and/or an alkoxysilyl group and also having an amino-containing group in a side chain;
applying the coating layer composition to an elastic molded body; and
coating the elastic molded body with the coating layer composition,
wherein the amino-modified silicone compound has:
siloxane-repeating units represented by the following chemical formula (1)

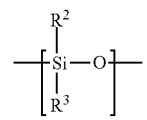

(1)

wherein in the chemical formula (1), -R² and -R³ are independently an alkyl group having 1-3 carbons or a phenyl group;
siloxane-repeating units having the amino-containing group and which are represented by the following chemical formula (2

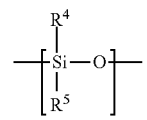

(2)

wherein in the chemical formula (2),
R⁴ is an alkyl group having 1-3 carbons or a phenyl group;
R⁵ is -U¹-N(—Rᵃ)-V¹-N(—Rᵇ)-W¹-NH(—Rᶜ), or -U²-N(—Rᵈ)-V²-NH(—Rᵉ), wherein -U¹-, -U²-, -V¹-, -V²- and -W¹- are —(CH₂)ₓ—, where x is a number of 2-4, or —(CH₂)ᵧ₁—(CH(CH₃))ᵧ₂—(CH₂)ᵧ₃—, where y1 and y2 are a number of 0-4 and y3 is a number of 1-4, and -Rᵃ, -Rᵇ, -Rᶜ, -Rᵈ, and -Rᵉ are independently a hydrogen atom, —(CH₂)_z—CH₃, where z is a number of 0-3, or —(CH₂CH(OH)CH₂(OH)); and silanol units having the silanol group and/or alkoxysilyl group which are represented by the following chemical formula (3)

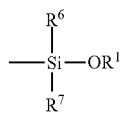

(3)

wherein in the chemical formula (3),
R¹ is a hydrogen group, a methyl group, an ethyl group, or a n-propyl group;
R⁶ is an alkyl group having 1-3 carbons, or a phenyl group; and
R⁷ is an alkyl group having 1-3 carbons, a phenyl group, or a binding moiety.

11. The method for manufacturing sliding member according to claim 10, comprising further adding an alkali ingredient into the coating layer composition.

* * * * *